United States Patent [19]

Shoher et al.

[11] Patent Number: 4,676,751
[45] Date of Patent: Jun. 30, 1987

[54] A METAL COMPOSITE FOIL, COPING, AND GROWN FOR A CERAMO-METAL DENTAL RESTORATION

[76] Inventors: Itzhak Shoher, 50 Shlomo Hamelech St., Tel Aviv; Aharon E. Whiteman, 13J1 Perez St., Petach Tikvah, both of Israel

[21] Appl. No.: 847,228

[22] Filed: Apr. 2, 1986

Related U.S. Application Data

[63] Continuation of Ser. No. 690,650, Jan. 11, 1985, abandoned.

[51] Int. Cl.⁴ .............................................. A61C 5/08
[52] U.S. Cl. .................................. 433/222; 428/607; 428/669; 433/218
[58] Field of Search ............... 433/207, 208, 218, 222, 433/223, 227; 428/607, 669, 670, 672, 621, 632; 228/263.18; 3/1.9

[56] References Cited

U.S. PATENT DOCUMENTS

| 431,848 | 7/1890 | Meyer | 428/669 |
| 1,397,063 | 5/1921 | Van Allen | 428/669 |
| 2,303,497 | 12/1942 | Reeve | 428/669 |
| 3,934,348 | 1/1976 | Janjii | 433/222 |
| 3,981,723 | 9/1976 | Toccillo | 433/207 |
| 4,123,262 | 10/1978 | Cascone | 433/207 |
| 4,218,244 | 8/1980 | Knosp | 433/207 |
| 4,273,580 | 6/1981 | Shoher et al. | 433/207 |
| 4,427,501 | 1/1984 | Rogers | 3/1.9 |
| 4,434,211 | 2/1984 | Shoher et al. | 428/553 |
| 4,459,112 | 7/1984 | Shoher et al. | 433/222 |
| 4,492,579 | 1/1985 | Shoher et al. | 433/222 |

FOREIGN PATENT DOCUMENTS

| 654818 | 12/1962 | Canada | 204/47 |
| 180142 | 10/1983 | Japan | 433/207 |
| 2133041A | 7/1984 | United Kingdom | 204/47 |

Primary Examiner—L. Dewayne Rutledge
Assistant Examiner—John J. Zimmerman

[57] ABSTRACT

A dental crown restoration which comprises a metal coping and a relatively thick outer coating of a ceramic dental veneer. The metal coping is composed of a lamination of a low fusing temperature precious metal component substantially or entirely of gold and a high fusing temperature precious metal component. The high fusing component is formed from three layers with one layer composed of from 90 to 100% palladium bounded on both sides by a gold based layer.

17 Claims, 5 Drawing Figures

A METAL COMPOSITE FOIL, COPING, AND GROWN FOR A CERAMO-METAL DENTAL RESTORATION

This application is a continuation of application Ser. No. 690,650 filed Jan. 11, 1985 and now abandoned.

This invention relates to the field of dental restorations and more particularly to an improved jacket crown and metal coping for a ceramo-metal crown restoration.

BACKGROUND OF INVENTION

A new technique for constructing a porcelain to metal crown having a fracture resistance comparable to or greater than the fracture resistance to impact forces of the veneer cast metal crown and which overcomes many of the shortcomings of the conventional porcelain jacket crown is disclosed in U.S. Pat. Nos. 4,273,580 and 4,459,112, respectively. In accordance with U.S. Pat. No. 4,273,580, a precious metal foil, preferably a laminate of several precious metal layers, is swaged about a prepared die of a tooth to form a metal matrix upon which a veneering material such as porcelain is fired. However, unlike the conventional porcelain jacket crown, the metal matrix is not removed or separated from the veneering material but is instead retained as a metal coping for the finished porcelain jacket crown. The metal coping is employed as an understructure for the jacket crown comparable in function to the cast metal understructure in the conventional porcelain to metal cast crown.

The physical strength of the metal coping may be substantially enhanced and the ease of preparing the restoration greatly simplified by converting the metal foil starting material into a preformed coping of predetermined geometry as taught and described in U.S. Pat. No. 4,459,112 referred to above. The metal foil starting material is cut into a circular segment and folded to form multiple pleats which are uniformly spaced apart and preferably extend radially from a central unfolded area. This multiple fold geometry makes it easy to adapt the preformed coping to the die without the need for superior skill and craftsmanship and even more importantly increases the rigidity and strength of the coping.

In each of the patents referred to above, the preformed coping is formed from a metal foil starting material preferably in the form of a laminated composite of at least two layers of precious metal or precious metal alloy. One of the layers is composed of a high fusing temperature precious metal such as platinum whereas the other is composed of a lower fusing temperature gold based metal composition substantially or entirely of gold.

The ability to adapt and swage the preformed coping to the die depends upon the flexibility and workability of the composite of metal layers from which the coping is formed and, in turn, is a measure of the softness of the metal foil. Conversely, the strength of the coping after it is swaged and removed from the die is dependent upon the hardness and rigidity of the coping. The hardness or softness of a metal is determined by measuring its resistance to permanent identation. A hardness number is assigned to the material using any one of several conventional hardness tests such as the Vickers hardness test which uses a diamond pyramid indenter. A dental coping should accordingly be sufficiently soft to adapt to the die and provide a close marginal fit and yet be hard and rigid after adaptation to provide strength.

SUMMARY OF THE INVENTION

In accordance with the present invention a layer composed of at least 90% palladium, which is a soft readily workable precious metal having a low Vickers hardness number, is preferably placed between two gold based layers to form a laminated composite representing the high fusing temperature component of the metal foil starting material. It was discovered that this combination of materials will function before sintering as a soft material and after sintering will convert to a harder and more rigid material. Moreover, it was further discovered that the gold based layers should be of substantially equal composition and symmetrically disposed about the palladium layer. Such an arrangement increases the fracture resistance of the composite and minimizes and distortion from differences in thermal expansion of the metals during heat treatment.

The dental jacket crown of the present invention comprises a metal foil coping composed of a low fusing temperature precious metal component substantially or entirely of gold superimposed upon a high fusing temperature component with the high fusing temperature component preferably including at least three layers in a laminated arrangement with one layer composed of from 90 to 100% palladium and being bounded on both sides by a substantially identical layer composed of a gold based composition of from 50 to 100% gold and with said crown having a relatively thick outer coating of a dental veneering material covering all or part of the metal foil.

The dental coping of the present invention preferably comprises a metal foil in a prefolded configuration and being composed of a low fusing temperature precious metal component substantially or entirely of gold superimposed upon a high fusing temperature component with the high fusing temperature component including at least three metal layers in a laminated arrangement with one layer composed of from 90 to 100% palladium and being bounded on both sides by a substantially identical layer composed of a gold based composition of from 50 to 100% gold.

OBJECTS AND BRIEF DESCRIPTION OF THE DRAWINGS

It is the principal object of the present invention to provide a dental crown with increased strength and resistance to fracture.

It is a further object of the present invention to provide a dental coping for a dental crown which is easily adapted to a die yet physically strong after swaging and dimensionally stable in response to heat treatment.

Other objects and advantages of the present invention will become apparent from the following detailed description of the invention when read in conjunction with the accompanying drawings of which:

DETAILED DESCRIPTION OF THE PREFERRED EMBODIMENT

Figure 1:
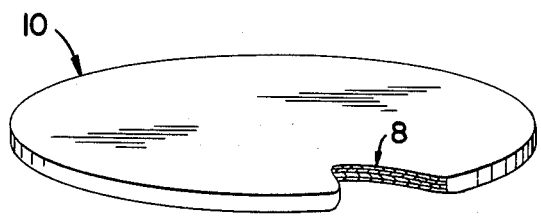
FIG. 1 is a perspective of the preferred metal foil starting material for forming the dental coping and jacket crown of the present invention.

The metal foil starting material 10 of FIG. 1 is composed of a low fusing temperature component 12 which is substantially or entirely of gold exclusive of minor impurities and a high fusing temperature component 14 which is superimposed on the low fusing temperature component 12 to form a lamination. The high fusing temperature component 14 is preferably made up of at least three layers 16, 18 and 20, respectively. The intermediate layer 16 is composed of from 90 to 100% palladium. Although palladium may be alloyed with other metals to form the intermediate layer 16, the alloyed product must still have a high fusing temperature of at least about 1300° C. and should have a low Vickers hardness number. It is, however, preferred, as will be explained in more detail hereafter, that the intermediate layer 16 be as close to pure palladium in its elemental state as is commercially obtainable. Palladium is commercially available at various refined levels of purity. Accordingly, a purity level of 99% or above is preferred with an optimum purity level of above 99.99%. The palladium layer 16 has a gold based metal layer 18 and 20 on each opposite side thereof which is substantially identical in thickness and composition. The gold based metal layers 18 and 20 contain from 50 to 100% gold and from 0 to 50% of one or more of the following elements in combination: silver, palladium, platinum, iridium, copper and aluminum with the latter two elements present, if at all, in small amounts relative to the other elements.

Figure 2:
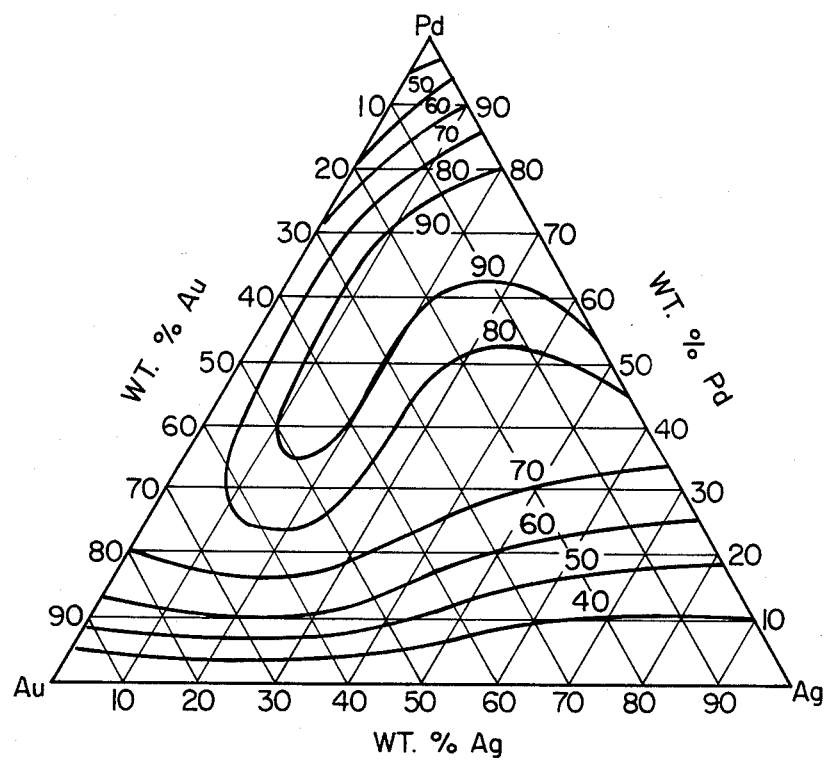
FIG. 2 is a conventional hardness graph for a ternary silver-gold palladium combination of precious metals.

The palladium layer 16 is a very soft material which as is shown in FIG. 2 has a Vickers hardness number of 40 for 100% Pd. It was discovered in accordance with the present invention that during heat treatment the metal foil material hardens to provide strength and rigidity. The hardening of the lamination is believed to be due to the diffusion of gold into the palladium layer from the opposing gold based layers. In accordance with FIG. 2 the hardness of 30–70% Au–70%–30% Pd is about 70 Vickers. Thus over a 50% increase in hardness is realized after heat treatment based on a 30% diffusion of gold into the palladium layer. This has been shown to be a reasonably expected level of diffusion.

The palladium layer 16 may also be made substantially thicker than the gold based layers 18 and 20 to provide substantially added body for the laminated structure without loss in pliability. A relatively thicker palladium layer is still readily workable in its soft condition before heat treatment and provides improved handling properties for the foil structure after heat treatment. The increase in hardness also increases the polishability of the cervical margin of the dental crown.

It is preferred that the palladium layer 16 be about at least twice as thick as the combined thickness of the adjacent gold based layers 18 and 20.

The palladium layer 16 may have a thickness of between 15 to 30 microns with 25 microns being preferred whereas the gold based layers 18 and 20 may be very thin, e.g., between 4–9 microns with 6 microns being preferred.

The location of the palladium layer 16 between two substantially identical gold based layers 18 and 20, is important to establish dimensional stability in response to heat treatments and after porcelain baking. The likelihood of distortion from thermal expansion during this heat treatment operation is reduced and the resistance of the crown to fracture from the heat treatment operation is increased.

Figure 3:
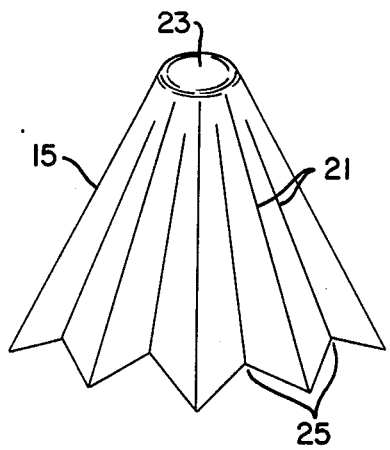
FIG. 3 is a perspective of the preferred dental coping of the present invention formed from the starting material of FIG. 1.

The metal foil starting material 10 is preferably first formed into a prefolded coping 15, as shown in FIG. 3, before being adapted to a die following the procedure taught and described in U.S. Pat. No. 4,459,112 which is herein incorporated by reference. As described in the patent, the metal foil starting material 10 is cut into a blank of circular geometry and folded to form multiple fold lines 21. The fold lines 21 extend from a central unfolded area 23 to form pleats 25. The coping 15 is then placed over the die (not shown) to adapt the coping to the die using any conventional swaging device. Once the coping is adapted and removed from the die, it is heat treated by placing it over the flame of a Bunsen burner for a short time period based on flame temperature to allow the low fusing temperature gold layer 12 to flow to form a compact metal matrix without air pockets. This heat treatment may also be carried out in a furnace at a temperature of about 1020° C. to 1150° C.

After the heating step, porcelain or another veneering material can be directly applied in a conventional manner to form the dental crown of the invention. It is desirable but not essential to coat the outside surface of the metal foil before the porcelain is applied with a bonding composition to achieve an unbreakable bond between the porcelain layers and the metal coping. A preferred bonding composition is taught and described in U.S. Pat. No. 4,434,211 which includes a gold based precious metal composition in combination with a halide of a noble metal such as a gold or silver chloride. The bonding material should be sintered to the metal coping at a temperature above 1600° F. which can be achieved simultaneously with the firing of the required porcelain outer layers. The heat treatment of the porcelain is conventional and any typical firing schedule may be applied with a firing temperature generally between 1600° F. to 1820° F.

Figures 1A, 4:
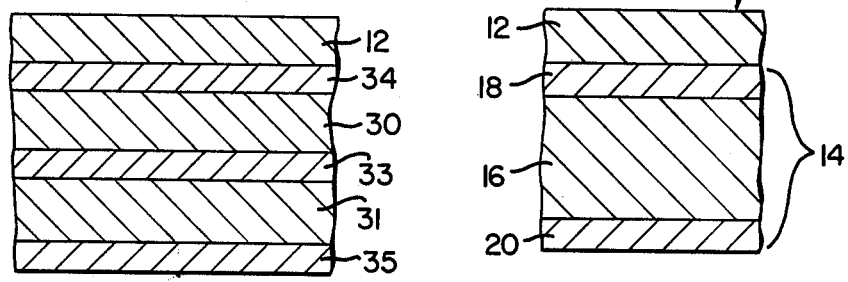
FIG. 1A is a magnified cross sectional view of the laminated metal foil starting material of FIG. 1.
FIG. 4 is a magnified cross sectional view of an alternative laminated arrangement relative to that of FIG. 1.

The present invention is not to be construed as limited to a high fusing component laminated arrangement with only one palladium layer preferably bounded on each side by a gold based layer. The same arrangement can readily be expanded to include two palladium layers bounded on each side by a gold based layer. Moreover, one of the gold based layers may be common to both palladium layers as shown in FIG. 4. Accordingly, as shown in FIG. 4, each palladium layer 30 is bounded on both sides by gold based layers 34 and 33 and palladium layer 31 is bounded on both sides by gold based layers 35 and 33. The low fusing component 12 would remain the same.

What we claim is:

1. A dental crown restoration comprising a metal coping composed of a low fusing temperature precious metal component substantially or entirely of gold superimposed upon a high fusing temperature component, with the high fusing temperature component including at least three layers in a laminated arrangement with one layer composed of from 90 to 100% palladium and with the palladium layer being bounded on both sides by a metal layer of substantially identical gold based metal composition having from 50 to 100% gold and a relatively thick outer coating of a dental veneering material covering all or part of the metal coping.

2. The dental crown of claim 1 wherein said palladium layer is substantially at least as thick as the thickness of both of said substantially identical layers of gold based metal composition.

3. The dental crown of claim 2 wherein said palladium layer is between 15-30 microns in thickness and wherein each gold based layer is between 4-9 microns thick.

4. The dental crown of claim 3 wherein each gold based layer is of substantially equal thickness.

5. The dental crown of claim 4 wherein said palladium layer is about 25 microns in thickness and each opposing layer of gold based metal is about 6 microns thick.

6. The dental crown of claim 4 wherein said palladium layer is at least 99% pure palladium.

7. A dental coping for use in preparing a dental restoration comprising a metal foil composed of a lamination of precious metals or metal alloys including a low fusing temperature precious metal lamina substantially or entirely of gold and a high fusing temperature laminated component defined by at least three layers with one layer composed of from 90 to 100% palladium and with the palladium layer being bounded on both sides by a layer of substantially identical gold based metal composition having from 50 to 100% gold.

8. A dental coping as defined in claim 4 wherein said palladium layer is substantially at least as thick as the thickness of both of said substantially identical layers of gold based metal composition.

9. A dental coping as defined in claim 6 wherein each gold based layer is of substantially equal thickness.

10. A dental coping as defined in claim 7 wherein said palladium layer is between 15-30 microns in thickness and wherein each gold based layer is between 4-9 microns thick.

11. A dental coping as defined in claim 10 wherein said metal foil is arranged in a prefolded geometry having multiple pleated sections.

12. A dental coping as defined in claim 7 wherein said metal foil is circular and has a central unfolded area with the pleated sections extending radially from the central unfolded area.

13. A dental coping as defined in claims 12 or 10 wherein said palladium layer is at least 99% pure palladium.

14. A metal foil for use in preparing a ceramo-metal dental restoration upon which a ceramic veneer is applied and fired in a furnace comprising a high fusing temperature precious metal component having at least one layer composed substantially or entirely of palladium and a low fusing temperature precious metal component composed substantially or entirely of gold disposed on opposite sides of said palladium layer.

15. A metal foil as defined in claim 14 wherein said palladium layer is substantially thicker than each gold layer.

16. A coping for use in preparing a ceramo-metal dental restoration having a ceramic veneer superstructure comprising at least one layer of a high fusing temperature precious metal component composed substantially or entirely of palladium, at least one layer of a low fusing temperature precious metal component composed substantially or entirely of gold and a layer of a precious metal alloy of said high fusing temperature precious metal component and said low fusing temperature precious metal component with said alloy layer disposed at the interface between said high and low fusing temperature precious metal layers and formed upon heat treatment of said coping in the preparation of said dental restoration at a temperature below the melting temperature of said high fusing temperature component.

17. A coping as defined in claim 16 wherein a low fusing temperature gold layer is disposed on each side of said high fusing temperature palladium layer and with an alloy of palladium and gold disposed on opposite sides of said palladium layer at the interface thereof and formed in response to heat treatment of said coping.

* * * * *